United States Patent [19]

Ismail

[11] Patent Number: 4,758,160
[45] Date of Patent: Jul. 19, 1988

[54] DENTAL IMPLANT

[75] Inventor: Yahia H. Ismail, Pittsburgh, Pa.

[73] Assignee: Isis International, Inc., Pittsburgh, Pa.

[21] Appl. No.: 932,616

[22] Filed: Nov. 20, 1986

[51] Int. Cl.$^4$ .............................................. A61C 8/00
[52] U.S. Cl. ................................... 433/173; 433/169; 433/174
[58] Field of Search ............... 433/173, 174, 175, 176, 433/169, 170, 201.1, 220, 221

[56] References Cited

U.S. PATENT DOCUMENTS

| | | | |
|---|---|---|---|
| 581,335 | 4/1897 | Carr | 433/174 |
| 3,473,222 | 10/1969 | Kester | 433/173 |
| 3,618,212 | 11/1971 | Weissman | 433/174 |
| 4,293,302 | 10/1981 | Hassler et al. | 433/173 |
| 4,552,532 | 11/1985 | Mozsary | 433/174 |
| 4,575,340 | 3/1986 | Lustig | 433/173 |

Primary Examiner—John J. Wilson
Attorney, Agent, or Firm—Webb, Burden, Ziesenheim & Webb

[57] ABSTRACT

A dental implant comprising an endosteal implant, having a bifurcated core therein, adapted for receiving a prosthetic head. The abutting surfaces of the endosteal implant and the prosthetic head preferably have equal outer diameters. The prosthetic head has a bifurcated shank thereon. The bifurcated core and bifurcated shank cooperate to secure the prosthetic head to the endosteal implant only at an inner segment of the bifurcated core, so as to preserve an annular space between the outer shank segment and the outer portion of the bifurcated core in the area of the alveolar bone. By means of this specialized attachment of the prosthetic head to the endosteal implant, stresses applied to the prosthetic head are translated directly to an inner segment of the endosteal implant, and thus are not applied to the alveolar ridge. Cratering of the alveolar bone is minimized as a result.

17 Claims, 1 Drawing Sheet

DENTAL IMPLANT

FIELD OF THE INVENTION

The present invention relates to mandibular or maxillary implants for the temporary or permanent retention of artificial dentures and related prostheses.

INTRODUCTION

Mandibular and maxillary bone implants, to which dentures and other structures are anchored, are increasingly widely used in restorative oral and maxillofacial surgery. Notwithstanding advances in this art, however, many implant arrangements unfortunately fail within a few years of implantation. Although this failure is generally due to physical, metabolic and other physiologic forces, many failures result specifically from "cratering" in the alveolar ridge bone tissue immediately adjacent the implant site. As a result, the development of improved dental implants, which enable bony union without alveolar ridge cratering, represents a much needed advance in the prosthodontic art.

BACKGROUND OF THE INVENTION

A number of dental implants are disclosed in various United States patents. U.S. Pat. No. 4,552,532 to Mozsary is directed to a dental implant system that includes a serrated cylindrical root 12 which is implanted into the jawbone and receives the threaded end of a crown support post 34. The crown 44 is supported directly by the conical shaped upper portion 40 of the crown support post 34. A resilient member 48 is placed between the root 12 and the post 34 in order to absorb or cushion forces which are applied to the crown 44.

In addition, a number of prior art patents disclose the use of resilient materials or structures as shock absorbing segments within a dental implant structure. Exemplary of these patents are U.S. Pat. Nos. 3,863,344 to Pillet, 3,934,347 to Lash et al., 4,081,908 to Sneer, 4,318,696 to Kasama et al., 3,827,145 to Richards, 4,215,986 to Reiss, and 4,416,629 to Mozsary et al.

Prior art devices fail to eliminate cratering of alveolar bone adjacent the implant, unfortunately, because even when such implants include resilient, shock-absorbing structures, the implant as a whole is nonetheless subject to rotational forces which cause greater stress to be applied to the alveolar ridge than is applied to the endosteal bone. At the same time, the periosteal surface of the alveolar bone is less able to withstand stress than is the endosteum. A need remains, therefore, for a dental implant which not only provides an implant receptor, in the general manner of prior art devices, but which also minimizes cratering in the alveolar bone in order to maximize permanence of the dental implant.

BRIEF DESCRIPTION OF THE INVENTION

In order to meet this need, the present dental implant comprises an endosteal implant, having a bifurcated core therein, adapted for receiving a prosthetic head. Preferably, the abutting surfaces of the endosteal implant and the prosthetic head have equal outer diameters. The prosthetic head has a bifurcated shank thereon. The bifurcated shank and the bifurcated core cooperate to secure the prosthetic head to the endosteal implant only at an inner segment of the bifurcated core, so as to preserve an annular space between the outer shank segment and the outer portion of the bifurcated core in the area of the alveolar bone. By means of this specialized attachment of the prosthetic head to the endosteal implant, stresses applied to the prosthetic head are translated directly to an inner segment of the endosteal implant, and are thus not applied to the alveolar ridge. Cratering of the alveolar bone is minimized as a result.

DETAILED DESCRIPTION OF THE INVENTION

Figure 1:
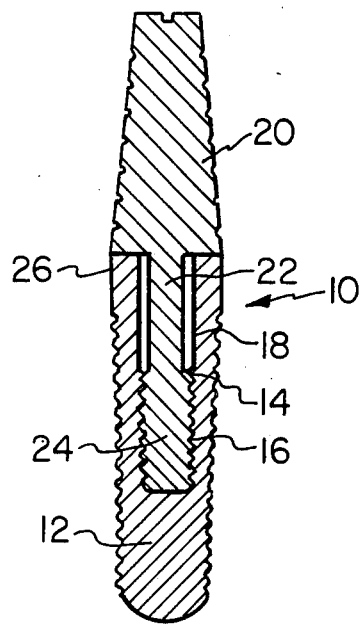
FIG. 1 is a sectional view of the dental implant 10, illustrating the endosteal implant and the prosthetic head.

Referring now to FIG. 1, the dental implant 10 of the present invention comprises an endosteal implant 12 and a prosthetic head 20 secured therewithin by means of shank 22. The endosteal implant 12 is serrated on its outer surface and has a bifurcated core 14 therein; after surgical implantation, the endosteal implant 12 is entirely embedded in mandibular or maxillary bone approximately up to the locus of bone surface 26. As shown, the abutting horizontal surfaces of the prosthetic head 20 and the endosteal implant 10 have equal outer diameters, as is preferred in the practice of the present invention.

The bifurcated core 14 has a threaded portion 16 and an alveolar portion 18; the threaded portion 16 is adapted to receive the threaded portion 24 of the shank 22 of the prosthetic head 20, and the alveolar portion 18 is adapted to receive the unthreaded portion of the shank 22. As a result of this structural combination, the threaded portion 24 of the shank 22 of the prosthetic head 20 is firmly affixed to the threaded portion 16 of the bifurcated core 14, whereas the alveolar portion 18 of the bifurcated core 14 does not touch and is annularly spaced away from the shank 22. In other words, only an inner segment of the bifurcated shank of the prosthetic head 20 is affixed to an inner segment of the bifurcated core of the endosteal implant 12; the respective outer segments, in the area of the alveolar bone, are annularly spaced apart to create an "annular space" or "annular area". By "inner," applicant refers to that segment of a structure which, as the structure is in position, is inward of the outer surface, or alveolar surface, of the endosteal implant.

The space remaining between the outer segment of the shank 22 and the outer segment of the bifurcated core 14 assures that minimal stress is applied to the alveolar bone by the implant arrangement. By referring to FIG. 1, it can be seen that any lateral (i.e., nonaxial)

forces on the prosthetic head 20 are translated directly to the threaded portion 16 of the bifurcated core 14, and do not translate to the alveolar portion 18 of the bifurcated core 14 for direct transmission to the alveolar bone. As a result, any nonaxial forces on the prosthetic head 20 are translated to the alveolar bone only by means of the rotation of the entire endosteal implant 12 which such forces may cause, but, as shown in FIG. 1, the area of attachment between the threaded portion 24 of shank 22 and the threaded portion 16 of the bifurcated core 14 is preferably in the center of the endosteal implant. Translation of force to the geometric center of the endosteal implant minimizes rotational forces which translate to the upper and lower ends of that structure, and stress application to the alveolar bone is minimized. Moreover, in this preferred embodiment of the invention, axial forces on the prosthetic head 20 are dispersed evenly over the endosteal implant 12 due to their equal outer diameters at their abutting surfaces.

Preferably, the annular space is at least 0.05 millimeter, preferably is at least 0.1 millimeter, and more preferably is 0.25 millimeter in width. The annularly spaced area need not be an actual void, but may be filled with fillers known in the art as long as the filler does not itself translate applied forces. Resilient fillers are therefore required in the practice of the present invention.

Figure 2:
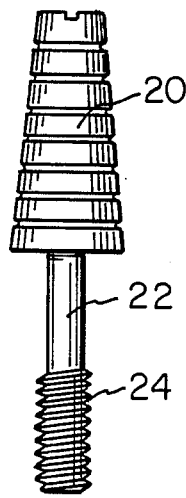
FIG. 2 is a side elevational view of the prosthetic head of FIG. 1.
Figure 3:
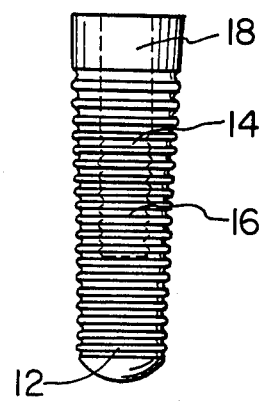
FIG. 3 is a side elevational view of the endosteal implant of FIG. 1.

FIGS. 2 and 3 illustrate in side elevational view the individual components of the dental implant 10 of FIG. 1. FIG. 2 is a side elevational view of the prosthetic head 20 having the shank 22 having a threaded portion 24 thereon; FIG. 3 illustrates the endosteal implant 12 having a bifurcated core 14 thereon, which core 14 has a threaded portion 16 and an alveolar portion 18.

Figure 4:
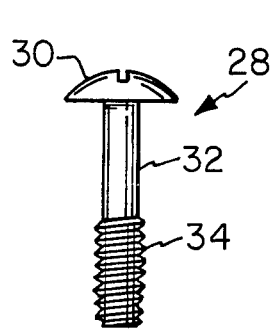
FIG. 4 is a side elevational view of a temporary healing cap.
Figure 5:
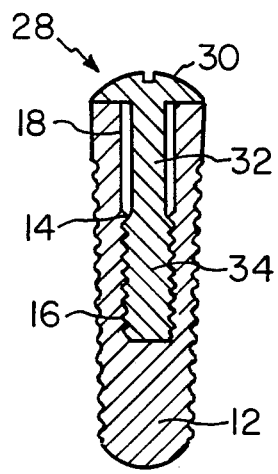
FIG. 5 is a sectional view showing the temporary healing cap of FIG. 4 in place in the endosteal implant of FIG. 1.

Referring now to FIG. 4, a healing cap 28 is disclosed having a healing cap head 30, a healing cap shank 32 and a healing cap shank, threaded portion 34. The healing cap, shown in position in the endosteal implant 12 in FIG. 5, is inserted immediately upon surgical implantation of the endosteal implant 12, and is left in place until the desired healing has taken place. The shank 32 and shank, threaded portion 34 of the healing cap 28 perform this same stress alleviation function on behalf of the alveolar bone as does the prosthetic head 20 of FIGS. 1-3.

Figure 6:
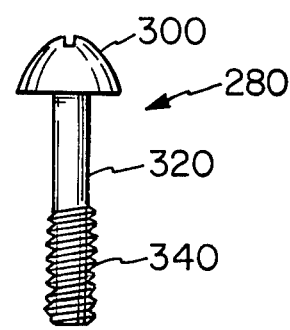
FIG. 6 is a side elevational view of an alternate healing cap.

FIG. 6 illustrates an alternate healing cap 280 having an alternate healing cap head 300, an alternate healing cap shank 320 and an alternate healing cap shank, threaded portion 340. The alternate healing cap 280, except for the variance in the shape of the head 300, has the same structure and performs the same function as does the healing cap 28 of FIG. 4.

Figure 7:
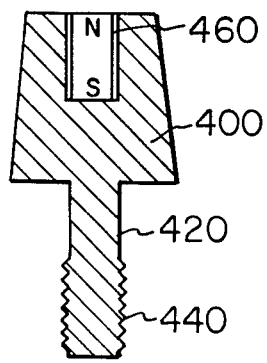
FIG. 7 is a sectional view of an alternate prosthetic head having a magnetic insert therein.
Figure 8:
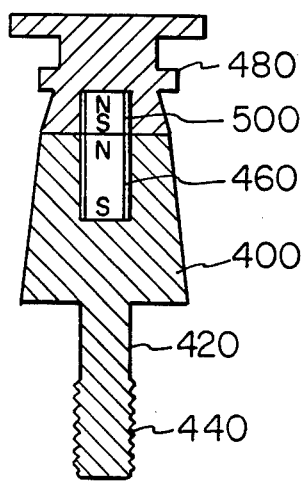
FIG. 8 is a sectional view of the alternate prosthetic head of FIG. 7 having a dental abutment having a magnet means in position thereon.

FIG. 7 illustrates an alternate prosthetic head 400, having a shank 420 and a threaded portion of shank 440 thereon, within which a magnetic insert 460 is mounted at its upper surface. As shown in FIG. 8, the alternate prosthetic head 400 is adapted for engaging a dental abutment 480 having magnet means 500 therein. The alternate prosthetic head 400 of FIGS. 7 and 8 is designed, by means of its two-part shank, to fit within an endosteal implant in the same manner as do the various shanks illustrated in FIGS. 1-6.

Materials suitable for use in the present dental implant are the alloys and polymers generally accepted for use in the dental implant art. However, because the present dental implant has particular stability and concommitant longevity in position, the avoidance of cytotoxic or otherwise biologically active structural materials is essential. For this reason, the biologically inert stainless steel and titanium alloys known in the implant art are the preferred materials for use in the present invention.

The dimensions of the embodiment of the invention illustrated in FIG. 1 are as follows, and are exemplary of the various dimensions which may be used in the present invention. The prosthetic head 20 is 8 millimeters in length; the shaft 22 thereon is likewise 8 millimeters in length. The narrowest diameter of the prosthetic head 20 is 2 millimeters; at its widest its diameter is 3.75 millimeters. The shaft 22 is 1.5 millimeters in diameter, with the threaded portion 24 of shaft 22 being 1.75 millimeters in diameter. The endosteal implant 12 is 12 millimeters in length; the core 14 therein is 8 millimeters in length. The core 14 has an internal diameter of 1.75 millimeters throughout its entire diameter. The outer radius of the endosteal implant 12 at its widest point is 3.75 millimeters. Alternately, and only by way of additional example, the endosteal implant 12 may be 10, 16 or 20 millimeters in length as needed, or may have a diameter at its widest point of 3.25 millimeters.

Notwithstanding the preferred and alternate embodiments of the invention illustrated in the Figures and described above, the present invention is susceptible of widespread adaptation without sacrifice of the advantages of its inventive features. The attachment between the innermost segment of the endosteal implant core and the innermost segment of the shank of the prosthetic head may be by any affixing or bonding means known in the art; actual threaded surfaces are therefore not necessary. Neither need the affixed area be centered along the length of the endosteal implant, as long as the affixed area is set geometrically inward from the alveolar surface of the endosteal implant. The prosthetic head may have any shape whatsoever, including simple and complex curved surfaces in place of the frustoconical arrangement shown in the Figures. Finally, although exemplary dimensions have been outlined above, the dental implant arrangement may be made larger or smaller to accommodate particular patients and applications.

The preferred embodiment of the invention was subjected to testing according to the following Example.

EXAMPLE

The preferred embodiment of the invention, having the structure and dimensions as described above, was implanted in a conventional test substrate and was subjected to three-dimensional finite stress analysis in a testing laboratory. Loci of stress identified by that analysis were located predominantly within the boundaries of the endosteal implant itself. Only a small percentage of the stress loci appeared in the surrounding substrate.

For the purposes of comparison, a prior art implant was affixed within an equivalent substrate and was subjected to the same stress analysis protocol. A significant percentage of the stress loci identified were located outside the boundaries of the prior art implant, and moreover were apparent throughout all portions of the substrate sample.

The invention is therefore to be limited only insofar as is set forth in the accompanying claims.

I claim:

1. A dental implant, comprising: an endosteal implant having an alveolar surface and a hollow core therein, a prosthetic head having a shaft thereon, and a prosthesis, wherein said shaft comprises an inner segment and an outer segment, wherein said shaft is removably affixed to said endosteal implant by means of said inner segment at a point spaced inward from said alveolar surface, said outer segment being positioned within said hollow core so as to form an annular area between said outer segment and the surface defining said hollow core, said annular area containing a material consisting of a resilient filler having no capacity for translating applied forces, and further wherein said prosthetic head is fixedly attached to said prosthesis, whereby forces applied to said prosthesis translate directly to said endosteal implant at said point spaced inward from said alveolar surface, to minimize rotational forces and stress application to the alveolar bone.

2. The dental implant according to claim 1, wherein said hollow core and said shaft are equal in length.

3. The dental implant according to claim 1, wherein said inner segment of said shaft comprises one-half the length of said shaft.

4. The dental implant according to claim 3, wherein said inner segment of said shaft is adapted to affix to the inner one-half segment of said hollow core of said endosteal implant.

5. The dental implant according to claim 4 wherein said inner segments of said shaft and of said hollow core are cooperatively threaded.

6. The dental implant according to claim 5 wherein the midpoint along the length of the cooperatively threaded areas of said shaft and said hollow core is the midpoint along the length of the endosteal implant.

7. The dental implant according to claim 5 wherein the midpoint along the length of the cooperatively threaded areas of said shaft and said hollow core is nearer said prosthetic head than is the midpoint of the length of said endosteal implant.

8. The dental implant according to claim 5 wherein the midpoint along the length of the cooperatively threaded areas of said shaft and said hollow core is farther from said prosthetic head than is the midpoint of the length of said endosteal implant.

9. The dental implant according to claim 5 wherein said outer segments of said shaft and of said hollow core of said endosteal implant define an annular area of at least 0.05 millimeter.

10. The dental implant according to claim 5 wherein said outer segments of said shaft and said hollow core of said endosteal implant define an annular area of 0.25 millimeter.

11. The dental implant according to claim 1 wherein said prosthetic head has a generally frustoconical shape.

12. The dental implant according to claim 11 wherein said prosthetic head has a serrated outer surface thereon.

13. The dental implant according to claim 11 wherein said endosteal implant tapers from a maximum outer diameter at its outermost end to a minimum diameter at its tip.

14. The dental implant according to claim 13, wherein the maximum outer diameter of said endosteal implant equals the maximum outer diameter of the frustoconical prosthetic head.

15. The dental implant according to claim 14 wherein said prosthetic head and said endosteal implant are fabricated from one or more materials selected from the group consisting of biologically inert alloys of stainless steel and biologically inert alloys of titanium.

16. The dental implant according to claim 1 wherein said endosteal implant has a serrated outer surface thereon.

17. The dental implant according to claim 1 wherein the length of said prosthetic head, excluding the length of said shaft, is less than the length of said endosteal implant.

* * * * *